(12) United States Patent
Floeter et al.

(10) Patent No.: US 8,841,505 B2
(45) Date of Patent: Sep. 23, 2014

(54) PROCESS FOR MAKING A BOND BETWEEN A HYDROPHILIC AND A HYDROPHOBIC NONWOVEN

(75) Inventors: Stefan Floeter, Euskirchen (DE); Saif Hasan, Euskirchen (DE); Gabriele Stiehl, Schwalbach (DE); Joseph Leslie Grolmes, Madeira, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 283 days.

(21) Appl. No.: 13/345,840

(22) Filed: Jan. 9, 2012

(65) Prior Publication Data

US 2012/0184933 A1  Jul. 19, 2012

Related U.S. Application Data

(60) Provisional application No. 61/434,052, filed on Jan. 19, 2011.

(51) Int. Cl.
 *A61F 13/15* (2006.01)
 *B32B 37/00* (2006.01)
 *C09J 5/00* (2006.01)

(52) U.S. Cl.
 USPC ........... 604/367; 604/366; 604/370; 604/379; 604/378; 156/290; 156/324

(58) Field of Classification Search
 USPC .......... 604/367, 366, 370, 379, 378; 156/290, 156/324, 62.8, 291
 See application file for complete search history.

(56) References Cited

U.S. PATENT DOCUMENTS

| | | | |
|---|---|---|---|
| 6,679,869 | B1 | 1/2004 | Schlinz et al. |
| 2002/0095127 | A1 | 7/2002 | Fish et al. |
| 2007/0173153 | A1* | 7/2007 | Paul et al. .................... 442/149 |
| 2009/0266478 | A1 | 10/2009 | Schaefer et al. |

FOREIGN PATENT DOCUMENTS

| | | |
|---|---|---|
| EP | 0368102 A2 | 5/1990 |
| JP | 4-25444 | 1/1992 |
| JP | 2001-158074 A | 6/2001 |
| WO | WO 96/12461 | 5/1996 |

* cited by examiner

*Primary Examiner* — Jacqueline F. Stephens
(74) *Attorney, Agent, or Firm* — Kathleen Y. Carter

(57) ABSTRACT

A process is provided for making a bond between a first, relative hydrophilic nonwoven and a second relatively less hydrophilic nonwoven by use of a construction adhesive, by applying the adhesive only to the first more hydrophilic nonwoven; also provided are absorbent cores for absorbent article comprising such bonded nonwovens, and such absorbent articles.

14 Claims, No Drawings

PROCESS FOR MAKING A BOND BETWEEN A HYDROPHILIC AND A HYDROPHOBIC NONWOVEN

CROSS REFERENCE TO RELATED APPLICATIONS

This application claims the benefit of U.S. Provisional Application No. 61/434,052 filed on Jan. 19, 2011, which is herein incorporated by reference in its entirety.

FIELD OF THE INVENTION

The present disclosure relates to a process for making a bond between a first, relative hydrophilic nonwoven or first part thereof, and a second relatively less hydrophilic nonwoven or first part thereof, by use of a construction adhesive, by applying the adhesive only to the first more hydrophilic nonwoven or first part thereof. The present disclosure further relates to absorbent cores for absorbent articles comprising such bonded nonwovens, and such absorbent articles.

BACKGROUND OF THE INVENTION

Absorbent articles such as diapers or sanitary napkins typically comprise absorbent cores to store fluids discharged from the body. The absorbent cores typically comprise an absorbent material, enclosed by a core-wrap, e.g., a nonwoven material, sealed around the absorbent material.

Conventional absorbent cores typically comprise high amounts of cellulose fibers in combination with superabsorbent polymer particles wherein the cellulose fibers serve to immobilize the superabsorbent polymer particles. Both the cellulose fibers and superabsorbent particles are typically disposed between two layers of nonwoven webs which are sealed together at their edges in order to avoid loss of superabsorbent polymer particles.

In the recent years, absorbent cores have been developed which comprise little amounts of cellulosic material, or may be completely free of cellulosic material. In light of the decreasing amount of cellulose, other immobilization techniques needed to be developed. For example, the superabsorbent particles may be immobilized by adhesive in fibrous form (often referred to as microfibrous thermoplastic adhesive) which immobilizes the superabsorbent particles on the one hand, but still accommodates swelling upon fluid uptake.

One difference between conventional absorbent cores which comprise cellulose and the more recent cores comprising only little amounts of cellulose or are free of cellulose is that the latter are considerably thinner and denser. While this is generally desirable, the reduced void volume results in higher total expansion of the absorbent core with the consequence that the forces exerted on the core seals upon swelling of the absorbent cores are increased compared to conventional absorbent cores.

Accordingly, there is a need to improve the bond strength of the core seals, especially with regard to thin absorbent cores that, nevertheless, have high absorbent capacity, and/or that comprise little or no cellulosic material.

SUMMARY OF THE INVENTION

In a first aspect, a process is provided for bonding a first nonwoven material and a second nonwoven material wherein the bond is formed by a construction adhesive, and whereby the first nonwoven material is more hydrophilic than the second nonwoven material; the process comprising the steps of a. providing the first nonwoven material with a first part thereof, and advancing the first nonwoven material or the first part thereof to an adhesive application station with construction adhesive;
b. providing the second nonwoven material with a first part thereof;
c. applying with the adhesive application station the construction adhesive to the first nonwoven material or to the first part of the first nonwoven material;
d. advancing the second nonwoven material or a first part thereof of and the first nonwoven material, or the first part thereof, with the adhesive, to a bonding station;
e. bonding the first nonwoven material or first part of the first nonwoven material via the construction adhesive to the second nonwoven material or to the first part thereof.

The first part of the second nonwoven thus comprises no construction adhesive prior to the step e). In step c), the construction adhesive may be applied at an application temperature of at least 120° C., and in the bonding step e) the construction adhesive may have then a temperature of at least 30° C. less than the application temperature of step c). In some other embodiments, the time and/or distance between the adhesive application step/station and bonding step/station (e.g., applying pressure) is at least 0.2 seconds and/or at least 1 meter, respectively. It has been found that an improved bonding (with as limited adhesive as possible) is achieved by applying the hydrophobic construction adhesive to the more hydrophilic nonwoven material, before contacting it with the less hydrophilic nonwoven; it is believed that this may be required in order to allow enough time for the adhesive to bind to the more hydrophilic nonwoven, e.g., to wrap around the more hydrophilic fibers thereof. In particular when the adhesive is applied as a melt (so-called hotmelt adhesive) and then allowed to cool down, for example even below the melt temperature, it has been found important to allow it to bind to the more hydrophilic nonwoven material in molten state, before binding it to the less hydrophilic nonwoven material. This cool down is for example achieved when there is a significant time/distance between the application and bonding stages, as described herein after.

In some embodiments herein, the first part of the first nonwoven material is or are the peripheral edge or edges thereof, and the first part of the second nonwoven material is or are the peripheral edge or edges thereof, and whereby in step c) the adhesive is applied to the first part of the first nonwoven material and the first part of the first nonwoven material is bonded in step e) to the first part of the second nonwoven material, and whereby the bond formed by the process are the bonded peripheral edge or edges of the first and second nonwoven materials. The first nonwoven material may have a second part, adjacent the first part and the second nonwoven material may have a second part, adjacent the first part, and the second part of the first nonwoven material and/or the second part of the second nonwoven material may carry a superabsorbent material. The first parts of the first and second nonwoven material may then for example both transverse (CD) peripheral edges, and optionally also one or two longitudinal (MD) peripheral edges, so that the second part is enclosed by at least the transverse edges and optionally also the longitudinal edge or edges, and hence, when the second part or second parts comprises superabsorbent material, the material is enclosed by first parts of the first and second nonwoven, i.e., the transverse edges and optionally the longitudinal edge or edges.

The superabsorbent material may for example be immobilized onto the second part of the second nonwoven material and/or onto the second part of the first nonwoven material by a further adhesive material, for example a fibrous adhesive material, e.g., applied as a fibrous adhesive over the superabsorbent material after applying the superabsorbent material onto the second part of the nonwoven material and/or onto the second part of the first nonwoven material, and the further adhesive typically being applied before step e).

In some embodiments herein, the second part of the first nonwoven material, and optionally the second part of the second nonwoven material may thus for example comprises no adhesive material, except optionally some of the fibrous adhesive material applied over the superabsorbent material.

In some embodiments, the second part of the second nonwoven material comprises no adhesive other than optionally the further fibrous adhesive applied over the superabsorbent material to immobilize it. In some embodiments, it may be preferred that the second nonwoven material comprises, prior to the binding step e), neither the construction adhesive material on the first part thereof, nor on the second part thereof, and it may optionally only comprise some of the fibrous adhesive material applied over the superabsorbent material.

The first nonwoven material may for example comprise fibers that are treated with a hydrophilic agent prior to nonwoven material formation, and/or the first nonwoven material is treated with a hydrophilic agent for example those described herein, including for example the described surfactant or mixtures thereof.

The present disclosure also relates to bonded first and second nonwoven material obtainable by the processes disclosed herein, and absorbent cores obtainable by the processes disclosed herein and absorbent articles comprising the absorbent core obtainable by the processes disclosed herein.

Alternatively, or in addition, the present disclosure relates to bonded first and second nonwovens, as further described herein, and absorbent cores, as further described herein, whereby the construction adhesive is present substantially around the fibers of the first, more hydrophilic nonwoven material, or of the first part thereof, as described herein, and not substantially around the fibers of the second, less hydrophilic nonwoven material or of the first part thereof, after bonding, typically the construction adhesive after bonding only being present on the surface of the second nonwoven material, or first part thereof, and hence substantially only on the part of the fibers of the second nonwoven material, forming the surface of the nonwoven.

It is believed that in order to provide a further improved bond, the first nonwoven, and optionally the second nonwoven may be a pattern bonded laminate nonwoven material, e.g., a pattern bonded laminate of at least one meltblown nonwoven layer, and at least one carded or spunbond nonwoven layer, or for example, a pattern bonded laminate of a meltblown layer sandwiched between at least two spunbond nonwoven layers.

DETAILED DESCRIPTION OF THE INVENTION

As used herein, the following terms have the following meanings:

"Absorbent article" herein refers to an article generally capable of absorbing and storing exudates discharged from the body, in an absorbent core thereof. Absorbent articles are typically placed against or in proximity to the body of a wearer to absorb and contain the exudates discharged from the body, such as urine, blood or menses in an absorbent core thereof. Typical absorbent articles include infant and adult diapers, including pant-like diapers and so-called taped diapers (e.g., with fastening elements to fasten the diaper about the lower torso of the wearer), diaper insert, diaper liners, feminine hygiene products, such as sanitary napkins, tampons or panty liners, and adult incontinent pads. "Diaper" refers to an absorbent article that is intended to be worn by wearer about the lower torso to absorb and contain exudates discharged from the body. Generally, pant-like diapers are placed in position on the wearer by inserting the wearer's legs into the leg openings and sliding the pant-like diaper into position about the wearer's lower torso.

"Absorbent core" refers to a member of an absorbent article that is intended to absorb and store exudates discharged from the body, e.g. urine or blood. The absorbent core according to the present disclosure comprises at least superabsorbent material, and the first, relatively more hydrophilic nonwoven material and the second nonwoven material, bonded by the process herein.

First Nonwoven Material and Second Nonwoven Material

The process herein binds a first, relative hydrophilic nonwoven material, or typically a first part thereof, to a second, relative less hydrophilic nonwoven material, or typically to a first part thereof. For the purpose of the invention, relatively more hydrophilic when used with respect to the first nonwoven material means that this material is more hydrophilic compared to the second nonwoven material; and, relatively less hydrophilic with respect to the second nonwoven material, means that this materiel is less hydrophilic than the first nonwoven material. The first nonwoven material and second nonwoven material may be unitary, whereby the first nonwoven material as referred to herein is then the first portion of the unitary nonwoven material and the second nonwoven material as referred to herein is then the second portion of the unitary nonwoven, and the unitary nonwoven is folded with a C-fold or Z-fold, so that the first portion, or first part thereof, and second portion or first part thereof, are bonded by the process herein. In such a case, the first portion may be treated to be more hydrophilic than the second portion, for example with the hydrophilic agents described herein below, or the second portion may be treated to be less hydrophilic than the first portion.

However, an alternative embodiment herein, the first nonwoven material and second nonwoven materials are not unitary and hence separate materials prior to bonding by the process herein.

The hydrophilicity of the first and second material may be expressed as, or determines by, the average strike-trough-time of the respective material, e.g., the time for a selected fluid (e.g., 0.9% saline) to pass through the nonwoven, as described herein below.

Typically, the first nonwoven material has an average strike through time (third gush) with is at least 30% less than the average strike through time (third gush) of the second nonwoven material. This difference may be at least 50%, or for example at least 100%, or for example at least 200%, or for example at least 300%. The strike through times (for first, second and third gush) and averages, and percentages difference thereof, can be determined by use of Edana method 150.3-96, with the difference that 3 gushes of 5 ml are applied with 60 seconds interval (rather than a single gush) and that 10 plies of filter paper are used (rather than 5); suitable equipment for these measurement is for example a Lister AC#86.

The first nonwoven may have an average strike through time (third gush) which is for example less than 25 seconds, or less than 10 seconds; the second nonwoven may for example have an average strike through time (third gush) of more than 50 seconds, or for example more than 100 seconds, or more than 200 seconds.

"Nonwoven material" as used herein refers to a manufactured material of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The basis weight of nonwoven materials is usually expressed in grams per square meter ($g/m^2$) and can be determined according to EDANA method 40.3-90. Nonwoven materials herein may comprise natural fibres synthetic fibres, or combinations thereof. Example natural fibres include but are not limited to: animal fibers such as wool, silk, fur, and hair; vegetable fibres such as cellulose, cotton, flax, linen, and hemp; and certain naturally occurring mineral fibres.

Exemplary synthetic fibers, which are derived from natural sources include but are not limited to viscose, polysaccharides (such as starch), rayon and lyocell. Exemplary fibers from mineral sources, i.e. petroleum, include but are not limited to polyolefin such as polypropylene or polyethylene) fibers and polyester fibers, whereby in some embodiments polypropylene may be preferred, and/or bicomponent fibres, for example of two of the polymer types referred to before.

Nonwoven materials can be formed by direct extrusion processes during which the fibers and webs are formed at about the same point in time, or by preformed fibers which can be laid into webs at a distinctly subsequent point in time. Exemplary direct extrusion processes include: spunbonding, meltblowing, solvent spinning, electrospinning, and combinations thereof. Nonwoven materials often comprise several layers, e.g., they may be nonwoven laminates, whereby the layers, or part thereof, may be made of different processes, as described herein.

As used herein, the term "spunbonded fibers" refers to small diameter fibers, which are formed by extruding molten thermoplastic material as filaments from a plurality of fine, usually circular capillaries of a spinneret. Spunbond fibers are quenched and generally not tacky when they are deposited onto a collecting surface. Spunbond fibers are generally continuous. The spunbond fibers herein may for example have diameters of from 10 µm up to 40 µm.

As used herein, the term "meltblown fibers" refers to fibers formed by extruding a molten thermoplastic material through a plurality of fine, usually circular, die capillaries as molten threads or filaments into converging high velocity gas (e.g., air) streams, which attenuate the filaments of molten thermoplastic material to reduce their diameter. Thereafter, the meltblown fibers are carried by the high velocity gas stream and are deposited on a collecting surface to form a web of randomly dispersed meltblown fibers. The meltblown fibers herein may for example have diameters of from 0.2 µm to less than 10 µm.

Example "laying" processes include wet-laying and dry-laying. Example dry-laying processes include but are not limited to air-laying, carding, and combinations thereof typically forming layers. Combinations of the above processes yield nonwovens commonly called hybrids or composites.

The total basis weight of the first nonwoven material and/or of the second nonwoven material used herein may be chosen such that it is high enough to ensure good area coverage and to provide sufficiently small pores. On the other hand the basis weight may be chosen such that it is not be too high, so that the nonwoven is still compliant and nonirritating to the skin of the wearer. In some embodiments, the total basis weight of the first nonwoven material may range from 6 to 20 $g/m^2$, or 8 to 16 $g/m^2$, or 8 to 14 $g/m^2$. The second nonwoven material may also have for example a basis weight within this range.

The first and second nonwoven materials herein include nonwoven laminate materials, made of two or more nonwoven layers that are laminated to one another, optionally via pattern bonding. The first and/or second nonwoven material may for example be a laminate of spunbond nonwoven layer and a melt blown nonwoven layer, or for example at least one meltblown nonwoven layer sandwiched between at least two spunbond nonwoven layers, hence at least one on either side of the meltblown layer. The first and/or second nonwoven material may, each independently, be a so-called SMS material, SMMS material, SSMMS, SMMMS, SSMMMS or the like.

The first nonwoven material and/or second nonwoven material may be pattern bonded, for example with a stripe pattern, or spiral pattern, a square pattern, or diamond shaped pattern; in particular the first nonwoven material may be pattern bonded laminate. It is believed that this may further improve the subsequent adhesive bonding.

The first nonwoven material is more hydrophilic than the second nonwoven material. It may thereto be made of fibres, that are made of polymers that are more hydrophilic than the polymers used for the fibres of the second nonwoven material, and/or fibres that have been treated with a treatment agent, such as a hydrophilic agent, rendering the fibres of the first nonwoven material more hydrophilic than the fibres of the second less hydrophilic nonwoven material. Alternatively, or in addition, the first nonwoven material is more hydrophilic due to the fact that the first nonwoven material is (after nonwoven formation) treated with a hydrophilic agent.

Such hydrophilic agents may for example include or be a surfactant, to render the first nonwoven material more liquid pervious.

Furthermore, it has been found that it may be beneficial that the hydrophilic agent comprises or is an aminopolyether-modified trialkoxysilane. The aminopolyether-modified trialkoxysilane is believed to provide a durable layer (e.g., coating) through cross-linking siloxane groups that bond the coating to the surface of a nonwoven material, and alkoxy groups which confer hydrophilicity.

Exemplary aminopolyether-modified trialkoxysilanes include, but are not limited to, polyether moieties having an epoxy endcapped polyether with the average structure $CH_2(O)CHCH_2(OCH_2CH_2)_{6.9}OCH_2CH(O)CH_2$ or $CH_2(O)CHCH_2(OCH_2CH_2)_{11.7}OCH_2CH(O)CH_2$. Other aminopolyether-modified trialkoxysilanes and methods of making them may include the hydrophilic agents disclosed in U.S. Patent Application Publication No. 2009/0117793 to Falk et al., and U.S. Patent Application Publication No. 2009/0118421 to Falk. For example, aminopolyether-modified trialkoxysilanes may include polyether moieties of the formula:

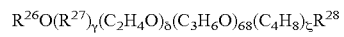

$$R^{26}O(R^{27})_\gamma(C_2H_4O)_\delta(C_3H_6O)_{68}(C_4H_8)_\zeta R^{28}$$

where $R^{26}$ and $R^{28}$ are independently a monovalent hydrocarbon radical containing one or more oxirane or oxetane moieties having from 3 to 12 carbon atoms; $R^{27}$ is selected from the group of divalent radicals consisting of —$C_2H_4O$—, —$C_3H_6O$—, and —$C_4H_8O$—; the subscript γ is zero or 1; the subscript δ is zero or positive and has a value ranging from 50 to about 100; the subscript ε is zero or positive and has a value ranging from 0 to about 100; and the subscript ζ is zero or positive and has a value ranging from 0 to about 100 subject to the limitation that the molecule remains polar.

Non-limiting examples of alternative or additional hydrophilic agents include nonionic and amphoteric surfactants such as Gemini diol ethoxylates, nonionic surfactants of Hydrophilic-Lipophilic Balance (HLB) between 3 and 16, the $C_{12}$-$C_{18}$ alkyl ethoxylates ("AE") including the narrow peaked alkyl ethoxylates and $C_6$-$C_{12}$ alkyl phenol alkoxylates (for example, ethoxylates and mixed ethoxy/propoxy), $C_{12}$-$C_{18}$ betaines and sulfobetaines ("sultaines"), $C_{10}$-$C_{18}$ amine oxides, and the like. In one embodiment, the hydrophilic agent is or includes a nonionic surfactant sold under the trade name "DYNOL 604" by Air Products and Chemical, Inc. In another embodiment, the hydrophilic agent is or includes a nonionic surfactant sold under the trade name "DYNOL 607" by Air Products and Chemical, Inc. In another embodiment, the hydrophilic agent is or includes a nonionic surfactant sold under the tradename SURFYNOL™, by Air Products and Chemical, Inc, for example, Surfynol 420, Surfynol 440, Surfynol 465, or Surfynol 485. In another embodiment, the wetting agent is a nonionic surfactant sold under the tradename CARBOWET, by Air Products and Chemical, Inc, e.g., Carbowet 106, or Carbowet 109. And, in another embodiment, the hydrophilic agent is or includes a nonionic surfactant sold under the tradename NEODOL, by Shell Chemicals, for example, Neodol 91-6, Neodol 23-3, Neodol 1-9, Neodol 1-7, Neodol 91-8, or Neodol 45-7.

Another class of useful the hydrophilic agent includes silicone surfactants and/or silicones. They can be used alone and/or alternatively in combination with other hydrophilic agents, such as the alkyl ethoxylate surfactants described above. Nonlimiting examples of silicone surfactants are the polyalkylene oxide polysiloxanes having a dimethyl polysiloxane hydrophobic moiety and one or more hydrophilic polyalkylene side chains, and having the general formula:

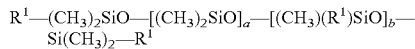

wherein a+b are from about 1 to about 50, and each $R^1$ is the same or different and is selected from the group consisting of methyl and a poly(ethyleneoxide/propyleneoxide) copolymer group having the general formula: —$(CH_2)_n O(C_2 H_4 O)_c (C_3 H_6 O)_d R^2$, wherein n is 3 or 4; total c (for all polyalkyleneoxy side groups) has a value of from 1 to about 100, alternatively from about 6 to about 100; total d is from 0 to about 14; alternatively d is 0; total c+d has a value of from about 5 to about 150, alternatively from about 9 to about 100 and each $R^2$ is the same or different and is selected from the group consisting of hydrogen, an alkyl having 1 to 4 carbon atoms, and an acetyl group, alternatively hydrogen and methyl group. Each polyalkylene oxide polysiloxane has at least one $R^1$ group being a poly(ethyleneoxide/propyleneoxide) copolymer group. Silicone surfactants are available from Dow Corning as silicone glycol copolymers (for example, Q2-5211 and Q2-5212), from Degussa, sold under the tradename TEGOWET, and from Momentive Performance Materials, sold under the tradename Silwet.

The hydrophilic agent may be applied at any desired amount to the fibers or first nonwoven material, for example, at least 0.05% or at least 0.1% by weight of the first nonwoven material, and typically less than 20% by weight, for example up to 10% or up to 5% by weight.

Construction Adhesive

The process herein applies a construction adhesive to the first more hydrophilic nonwoven material, or the first part thereof.

The adhesive may be any suitable adhesive, typically a hotmelt adhesive. It may be a hydrophilic adhesive. In some embodiments herein, it is a hydrophobic adhesive; it comprises at least a hydrophobic ingredient, such as an oil-based plasticizer.

In some embodiments herein, the adhesive is a hotmelt adhesive, that is applied as a melt at a temperature above its melting or softening point, for example above 120° C., or for example above 140° C. The adhesive can then more efficiently wrap itself about the fibers of the first nonwoven material, even if these are for the purpose of the present invention more hydrophilic. The bonding to the second less hydrophilic nonwoven is then done subsequently at a downstream bonding station, to allow time for the adhesive to fully bind to the first, more hydrophilic nonwoven material. The construction adhesive may for example have a softening point of below 120° C., below 110° C. or for example below 100° C.—as measurable via ASTM E-28-99 (with Glycerin).

The construction adhesive comprises for example a polymeric component having a molecular weight of 10.000 or more, e.g., a thermoplastic component. It may for example comprise an adhesive component selected from block copolymer comprising polystyrene blocks, polybutadiene blocks, polyisoprene blocks and/or polyethylene/butadiene blocks. Preferred may for example be polystyrene-polyisoprene block copolymers or polystyrene-polybutadiene block copolymers.

Other suitable construction adhesives include metallocene polyolefin based adhesives (mPO). Metallocene polyethylene polymers, for example, may be obtained through polymerizing ethylene monomer with α-olefin (e.g., butene, hexene, octene) using metallocene catalytic system, e.g. Ziegler-Natta catalyst.

Other suitable construction adhesives include amorphous poly-alpha-olefin polymers based adhesives (APAO). Amorphous poly-alpha-olefin polymers are well known to those skilled in the art and can be either homopolymers of propylene or copolymers of propylene with one or more α-olefin comonomer, such as, for example, ethylene, butene-1, hexene-1 and octene-1.

These polymers can be either homopolymers of propylene or copolymers of propylene with one or more α-olefin comonomer, such as, for example, ethylene, butene-1, hexene-1 and octene-1.

The adhesive may comprise any suitable tackifier, such as water-white tackifiers. The adhesive comprises typically a plasticizers, that may for example have a molecular weight of 5000 or less, or for example 2000 or less. As mentioned above, this may be an oil-based plasticizer, comprising an oil or oil derivative, such a paraffin oil or derivative thereof. The adhesive may also comprise for example an anti-oxidant. Suitable adhesives are for example from HB Fuller, such as HL1358LO.

In some embodiments herein, the construction adhesive that forms the bond of the process herein has for example a storage modulus (reflecting its rheology) G' at 20° C. of less than 110 kPa, or for example less than 100 kPa, or less than 90 kPa, but of more than 40 kPa, more than 50 kPa; and/or at 35° C. of less than 70 kPa, or less than 50 kPa, or for example less than 40 kPa, but for example of more than 10 kPa, or for example more than 15 kPa; and/or at 60° C. of less than 40 kPa, or less than 30 kPa, or for example less than 20 kPa, but for example of more than 5 kPa, or for example more than 8 kPa; and/or at 90° C. of less than 25 kPa, or less than 15 kPa, but of more than 3 kPa. This can be measured by the method as set out in EP-A-1447067.

Process for Making a Bond Between the First Nonwoven and Second Nonwoven Material According to the present disclosure, a bond is formed by use of a construction adhesive, for example a so-called hotmelt adhesive, described above. The process herein comprises the steps of:

a) providing the first nonwoven material with a first part thereof, and advancing the first nonwoven material or the first part thereof to an adhesive application station with construction adhesive;

b) providing the second nonwoven material with a first part thereof;

c) applying with the adhesive application station the construction adhesive to the first nonwoven material or to the first part of the first nonwoven material;

d) advancing the second nonwoven material or a first part thereof of and the first nonwoven material, or the first part thereof, with the adhesive, to a bonding station;

e) bonding the first nonwoven material or first part of the first nonwoven material via the construction adhesive to the second nonwoven material or to the first part thereof.

In some embodiments herein, the adhesive is applied to a first part of the nonwoven and the first part is bonded to the second nonwoven material, or to a first part of the second nonwoven, e.g., only to the first part of the first nonwoven material. It should be understood that the first part at least of the second nonwoven is thus free of adhesives herein.

The first nonwoven material may be an individual material, of any shape, such as a rectangular shape, or it may be a web of a multitude of individual shapes, such as rectangular, travelling in a machine direction, MD; the nonwoven material, or each such individual shapes, may have a transverse front edge and a transverse back edge and/or longitudinal (in MD) opposing side edge or edges. Then, the first part of the nonwoven sheet may be any one of the edges or combination thereof, including all of the edges. In some embodiments, the first part of the first nonwoven sheet are at least, or only, both the transverse front and back edges, and the adhesive is applied to the edges (e.g. only).

The second nonwoven material may be an individual material, of any shape, such as a rectangular shape, or it may be a web of a multitude of individual shapes, such as rectangular, travelling in a machine direction; the nonwoven material, or each such individual shapes, may have a transverse front edge and a transverse back edge and/or longitudinal (in MD) opposing side edges. Then, the first part of the nonwoven sheet may be any one of the edges or combination thereof, including all of the edges. In some embodiments, the first part of the second nonwoven sheet are both, or only, the transverse front and back edges, and the edges are bonded via the process herein, e.g. to the first part, e.g. the transverse front and back edge of the first nonwoven material.

Alternatively, or in addition, the longitudinal side edge or edges may of the first nonwoven may be bonded to the longitudinal edge or edges of the second nonwoven with the process herein.

Such transverse and/or longitudinal edge may for example be at least 3 mm, or at least 5 mm wide (average width) and for example along about the whole transverse or longitudinal dimension, respectively, of the nonwoven material.

In some embodiments, the transverse front edge of the first nonwoven material is bonded to the transverse front edge of the second nonwoven material, and the transverse back edge of the first nonwoven material is bonded to the transverse back edge of the second nonwoven material; in addition, or alternatively the longitudinal edge or edges of the first and second nonwoven material are bonded. In some embodiments, the first and second nonwoven material each have a second part, e.g., a central part, adjacent the edge or edges, or for example enclosed by at least the transverse edges and/or enclosed by at least the transverse edges and the one or both longitudinal edges. The second part of the first nonwoven, and/or the second part of the second nonwoven may then carry a superabsorbent material, as described herein after.

The second part of the first nonwoven material may for example not comprise any of such the construction adhesive. Alternatively, it may also comprise such an adhesive, in order to adhesive the superabsorbent material.

As described above, the first and second materials may be unitary, whereby one portion (first nonwoven material) is treated to be more hydrophilic than the second portion (second nonwoven material), and/or whereby the second portion (second nonwoven material) is treated to be less hydrophilic than the first portion (first nonwoven material); the unitary material is then folded with a C-fold or Z-fold, typically by a C-fold (e.g. with therein between the superabsorbent material carried by the second parts of the first and/or second nonwoven (i.e., portion). In such a case, the first part of the first nonwoven material (portion) may be a single longitudinal edge of the first nonwoven material, and/or the transverse edges, and the first part of the second nonwoven material (portion) may be a single longitudinal edge and/or the transverse edges, and the edges of the first nonwoven material and second nonwoven material (i.e., first and second portions) are then bonded by the process herein, to thus enclose the superabsorbent material between the nonwovens.

The adhesive may be applied to the first nonwoven or first part thereof uniformly, or in a pattern. It may be applied continuously or intermittently. If applied to the first part of the first nonwoven only, it may be intermittently or continuously applied over the part. It may for example be applied intermittently—in CD- and/or as an intermittent pattern in CD, for example as a multitude of MD extending stripes (spaced apart in CD) on the first part of the first nonwoven.

For example, the adhesive may be applied to the first nonwoven or to the first part of the first nonwoven, in a pattern of stripes of any width, for example, between 0.1 mm and 1 cm, or for example between 0.1 and 2 mm (with a distance between them that may also be within either of these ranges, respectively); or for example as a spiral or omega pattern.

In any event, it may be applied as any basis weight level of for example between 5 gsm and 75 gsm m or for example between 10 or 15 gsm and 40 or 30 gsm.

The adhesive may for example be applied by non-contact or contact processes, such as a spray nozzle, a spray gun, or by coating or printing processes, including slot coating. The adhesive is typically applied as a melt to the first nonwoven material, or first part thereof.

Then, the first and second nonwovens, or first parts thereof, are typically combined in a combining point, which may be just before or at the bonding station, but in any event after the adhesive application step. In any event they are combined and bonded such that the adhesive is sandwiched between the first nonwoven or first part thereof and second nonwoven or first part thereof.

The bonding step is a separate step, done in a bonding station that is therefore typically downstream from the adhesive application step/station. In some embodiments, the bonding step/bonding station is at least 1 meter, or at least 2 meter from the adhesive application step/station; and/or the open time (the time between application of adhesive and bonding) is at least 0.2 seconds, or for example at least 0.3 seconds or for example at least 0.5 seconds.

The bonding is for example done by applying a pressure onto the combined first and second nonwovens, or first parts thereof, sandwiching the adhesive. Any suitable pressure bonding equipment can be used, including for example rotating rolls. It may be done by use of patterned roll, to apply a patterned bond. The applied pressure may for example be between 1 bar and 7 bar, or for example up to 4 bar or up to 3.5 bar, or in some embodiments, up to 2.5 bar. Due to the improved bonding, the required bonding pressure may be reduced, or the amount of adhesive may be reduced, or both. It may be advantageous to apply the construction adhesive to the first, more hydrophilic nonwoven material at suitable temperature to enhance its adherence to the fibers of the hydrophilic nonwoven web. For example, the construction adhesive may be applied to the first more hydrophilic nonwoven material or first part thereof at a temperature of for example at least the melt temperature or softening temperature of the adhesive, so it is applied as a liquid to the first nonwoven, for example a temperature of at least 100° C., or at least 120° C., 140° C., and for example up to 220° C. or to 200° C.

The distance and/or travelling time between the adhesive application station and bonding station may be such that the adhesive temperature reduces below its softening or melting temperature and/or it reduces at least 20° C., or for example at least 30° C. or for example at least 40° C., or for example at least 50° C. or for example at least 60° C. or at least 70° C. or at least 80° C.

Absorbent Core

In one aspect, the first nonwoven material and/or the second nonwoven material carries a superabsorbent material, e.g., on a second part of the first nonwoven material and/or on a second part of the second nonwoven material, as described herein, and the bonding process herein serves to bind the first part of the first nonwoven material and the first part of the second nonwoven material, to seal or partially seal the superabsorbent material, as described above; this may be a complete seal along all peripheral edges or for example only the front and/or back transverse edge, as described herein.

The process herein can thus be used to make an absorbent core for an absorbent article. The absorbent core may be of rectangular shape, or alternatively the core may have curved longitudinal and/or transverse edges. For example, the core may be of an elliptical or hourglass shape.

In a typical embodiment of the absorbent core described herein is oriented such that its first planar side is oriented towards the wearer and its second planar side is oriented towards the garment of the wearer when the absorbent article is worn, the first side comprising the first nonwoven material, the second side comprising the second nonwoven material.

The superabsorbent material (also referred to as absorbent gelling material) is typically particulate, e.g., particulate superabsorbent polymeric material, of internally cross-linked and surface-crosslinked polyelectrolyte polymers, such as internally cross-linked and surface crosslinked polycarboxylates/polycarboxylic acid polymers, such as polyacrylate/polyacrylic acid polymers. The superabsorbent particulate material may have any coating known in the art to improve its performance/processability. It may have any suitable particle size distribution.

The superabsorbent material herein typically has a CRC of at least 10 g/g, by typically at least 20 g/g, or at least 35 g/g or for example at least 35 g/g, as measured via the Centrifuge Retention Capacity Standard Test WSP 241.2.

The absorbent core may, in addition, to the superabsorbent material, for example comprise pulp fibres. However, in some embodiments herein, the core comprises substantially no absorbent cellulose fibre or pulp. The core may alternatively or in addition comprise adhesive fibres, such as fibrous thermoplastic adhesives, that can serve to immobilise the superabsorbent material, as known in the art. This further adhesive material in fibrous form is for example applied over the superabsorbent material, after deposition of the superabsorbent material on the nonwoven material, to immobilise it thereon. This may be done such that it does not significantly touch the first nonwoven material and/or the second nonwoven material.

Typically, the superabsorbent material and the fibrous adhesive material, if present, are present on the second part of the first nonwoven material and/or on the second part of the second nonwoven material and not on the first part of the nonwoven material and the first part of the second nonwoven material, so that the bond formed between the first part of the first nonwoven material and first part of the second nonwoven material is free of superabsorbent material and free of the fibrous adhesive material.

In some embodiments herein, the second part of the first and second nonwoven material may be a central part of for example between 50% and 95% of the surface area of the respective nonwoven material. In some embodiment herein, the second part or parts may be free of any adhesive, except some non-substantial amounts of the fibrous adhesive, if present over the superabsorbent material.

The fibrous adhesive, or thermoplastic fibrous adhesive, may for example be applied at a basis weight of between 11 $g/m^2$ to 0.5 $g/m^2$ or between 11 $g/m^2$ to 3 $g/m^2$, and may be from 9 $g/m^2$ to 5 $g/m^2$. The adhesive fibres may for example have an average thickness of from 1 µm to 100 µm, or from 25 µm to 75 µm. Suitable fibrous adhesive materials are described in for example EP 1447067. A typical thermoplastic adhesive that may be fibrous can have a Brookfield viscosity measured according to the test method ASTM 12-3236/88 at 149° C., spindle 27.5 at 30 rpm, from 2100 cP to 2800 cP, for example 2500 cP. In some embodiments herein, the fibrous adhesive may for example have a storage modulus (reflecting its rheology) G' at 20° C. of less than 300 kPa, or for example less than 200 kPa, but of more than 60 kPa, more than 80 kPa; and/or at 60° C. of less than 200 kPa, or less than 150 kPa, but for example of more than 18 kPa, or for example more than 24 kPa, or for example more than 30 kPa. This can be measured by the method as set out in EP-A-1447067.

Typically a relatively low amount of fibrous adhesive material can be used, for example less than about 40 weight %, less than about 20 weight %, or less than about 10 weight % of the total weight of the superabsorbent material.

The absorbent core may be part of an absorbent article, such as those described above. Articles herein may have a topsheet and a backsheet, e.g., which each have a front region, back region and crotch region, positioned therein between. The absorbent core as described herein is typically positioned in between the topsheet and backsheet. Backsheets may be vapor pervious but liquid impervious. Some topsheet materials are at least partially liquid permeable, and at least partially hydrophilic; the topsheet may be an apertured topsheets. The topsheet may comprise a skin care composition, e.g., a lotion. Absorbent articles may be thin, having an average caliper (thickness) in the crotch region of less than 1.0 cm, less than 0.7 cm, less than 0.5 cm, or even less than 0.3 cm (for this purpose alone, the crotch region being defined as the central zone of the product, when laid out flat and stretched, having a dimension of 20% of the length of the article and 50% of the width of the article). The articles may have a relatively narrow crotch width, which increases the wearing comfort. Some articles may achieve a crotch width of less than 100 mm, 90 mm, 80 mm, 70 mm, 60 mm or even less than 50 mm, as measured along a transversal line with is positioned at equal distance to the front edge and the rear edge of the article, or at the point with the narrowest width. Fastening diapers herein may have a front waist band and a back waist band, whereby the front waist band and back waist band each have a first end portion and a second end portion and a middle portion located between the end portions, and whereby the end portions may comprise each a fastening system, to fasten the front waist band to the rear waist band or whereby the end portions may be connected to one another, and whereby the middle portion of the back waist band and/or the back region of the backsheet and/or the crotch region of the backsheet comprises a landing member, the landing member may comprise second engaging elements selected from loops, hooks, slots, slits, buttons, magnets. Some embodiments include hooks, adhesive or cohesive second engaging elements. It may be that the engaging elements on the article, or diaper are provided with a means to ensure they are only engage able at certain moments, for example, they may be covered by a removable tab, which is removed when the engaging elements are to be engaged and may be re-closed when engagement is no longer needed, as described above. Some diapers herein have one or more sets of leg cuffs with elastics and/or barrier cuffs, typically with elastics, as known in the art.

Bonded Nonwovens Hang Time

This test is to measure the bonding strength between two nonwovens, and in particular between two nonwovens that seal superabsorbent material therein between, so that the bonding strength is a measure to predict whether the nonwoven can withstand the swelling pressures of the superabsorbent material and the pressures exerted from baby. This method determines the strength of the bond (seal) by measuring how long the perimeter seal can withstand a constantly applied force.

Samples are prepared from a first and second nonwoven material, as described herein, that are bonded to one another along their transverse front edge (this being thus the first part as defined herein) by applying a total of 25 gsm adhesive and pressure bonding this; samples are prepared that are inside the scope of the invention having the adhesive applied on the more hydrophilic nonwoven material (sample A), and that are outside the scope of the invention, having adhesive applied to either the less hydrophilic nonwoven or part of the adhesive applied to the more hydrophilic nonwoven and part to the less hydrophilic nonwoven, and the bond strength is compared as follows:

First nonwoven material: SSMMS nonwoven laminate, treated with surfactant on the adhesive application side, having a basis weight of 10 gsm; available from Avgol Mocksville (US))

Second nonwoven material: SMS nonwoven, non-treated

Each sample of each nonwoven has a transverse dimension of 25.4 mm (width) and a longitudinal dimension of 70 mm (length; MD), with a defined transverse edge over the full width (25.4 mm) and over 5 mm (in MD). This can be cut for example with a 25.4 mm (1 inch) cutter, such as a JDC Precision Sample Cutter made by Thwings-Albert Instrument Company Philadelphia USA, cat#99, cut width 25.4 mm, accuracy at least +/−0.1 mm)

Adhesive: HL1358LO as available from HB Fuller.

The adhesive is applied in intermittent parallel stripe s(in MD) pattern at a temperature of 145° C. The adhesive is applied 15 mm from the edge and there is thus an adhesive-free area adjacent the edge where the two nonwovens are not bonded. Each adhesive stripe has a length of 35 mm (in MD) of and a width of 1 mm, with 1 mm between stripes A pressure of 2.2 bar is applied for sample A and B and 3.3 bar for sample C below, in each case about 3 seconds after adhesive application, and in an environment of about 20° C., to allow cool-down of the adhesive between application and bonding.

Samples A: first nonwoven and second nonwoven as above, 25 gsm adhesive as above, applied over the transverse edge surface area of the first more hydrophilic nonwoven material in parallel stripe pattern (striped in longitudinal dimension), and pressure bonded, 3 seconds after adhesive application by applying 2.2 bar pressure over transverse edge for 1 second Sample B: first nonwoven and second nonwoven as above, 25 gsm adhesive in total, as above, but 60% is applied over the transverse edge surface area of the first more hydrophilic nonwoven material in parallel stripe pattern (striped in longitudinal dimension), to obtain 15 gsm, and 40% is applied over the transverse edge surface area of the second less hydrophilic nonwoven material in parallel stripe pattern (striped in longitudinal dimension), to obtain 10 gsm, and pressure bonded, 3 seconds after adhesive application by applying 2.2 bar pressure over transverse edge for 1 second.

Sample C: first nonwoven and second nonwoven as above, 25 gsm adhesive as above, applied over the transverse edge surface area of the second less hydrophilic nonwoven material in parallel stripe pattern (striped in longitudinal dimension), and pressure bonded, 3 seconds after adhesive application by applying 3.3 bar pressure over transverse edge for 1 second.

A RT-10 room temperature (23° C.) Shear Tester with timer is used, (as available from ChemInstruments, 510 Commercial Drive, Fairfield, Ohio 45014-9797, USA); and Medium Binder Clips 25 mm Capacity #72050, available from Yihai Products (#Y10003).

A 200 g (+/−1 g) TW200 Shear Tester Weight with hook on top (to attach to the clip) is used, as available from Cheminstruments, 510 Commercial Drive, Fairfield, Ohio 45014-9797, USA.

The tester and clips and weights are set up in an area where there is no risk of vibration and where the temperature is constant at 23° C. (50% humidity) and the tester and samples have been at least 2 hours at this temperature of the environment before use.

The un-adhered edge of the second nonwoven (i.e., the 15 mm adhesive-free area along the edge) is attached to the clamp at the top of the instrument bar and a 200 g weight is attached to the second part of the second nonwoven that is not bonded to the first part of the first nonwoven. The 200 g weight is then lowered until the weight hangs freely. As soon as the weight is released, the timer is started and the hang time of the weight is measured—the timers will stop automatically once the sample weight has fallen. This is the Hang time for that sample at the specific test temperature. All tests are done at 23° C.—if the temperature deviates, a correction to T=23° C. has to be done via the calculations set out below.

This is repeated for 9 times per sample type (A, B and C), to obtain 10 results for sample A, 10 results for sample B and 10 results for sample C, and the average hang time per sample (in minutes) and standard deviation, and the natural logarithm (ln) thereof, and average and deviation thereof, can then be determined and reported; and the ln (hang time at 23° C.) and standard deviations can be calculated as follows:

$$\ln(t_{23°C.}) = \ln\left|\left(\frac{311}{\exp\left(\frac{20207}{T_a + 273} - 62.527\right)}\right) \cdot t_a\right| \quad (1)$$

$t_a$: actual hang time [min] at the temperature $T_a$
$T_a$: temperature [C] of the test equipment and the sample during the measurement

| Sample | A | B | C |
|---|---|---|---|
| ln($t_{23\,C.}$) and standard deviation | 5.0 (0.1) | 3.9 (0.1) | 2.6 (0.4) |

The same test is repeated with the same type of samples A, B and C (10 each), except that all samples were stored at 50° C. (50% humidity) for 2 weeks, and then cooled down to 23° C. prior to testing:

| Sample | A | B | C |
|---|---|---|---|
| ln ($t_{23\,C.}$) (after 2 weeks at 50° C. and cool down to 23° C.) and standard deviation | 6.3 (0.2) | 5.4 (0.3) | 4.9 (0.3) |

Thus, when bonding a more hydrophilic and a more hydrophobic nonwoven, a stronger bond is achieved by applying the adhesive to the more hydrophilic nonwoven, and furthermore, lower bonding pressures may be used to obtain the improved bond. Furthermore, the improved bonding remains also after storage of the samples at elevated temperatures. Thus, an addition benefit is that reduced levels of adhesive may be used in the product and process of the invention to obtain the same or even better nonwoven bonding as could be achieved with much higher levels of adhesive applied to the more hydrophobic nonwoven.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."0

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Process for bonding a first nonwoven material and a second nonwoven material wherein the bond is formed by a construction adhesive, and whereby the first nonwoven material is more hydrophilic than the second nonwoven material; the process comprising the steps of
   a) providing the first nonwoven material with a first part thereof, and advancing the first nonwoven material or the first part thereof to an adhesive application station with construction adhesive;
   b) providing the second nonwoven material with a first part thereof;
   c) applying with the adhesive application station the construction adhesive to the first nonwoven material or to the first part of the first nonwoven material;
   d) advancing the second nonwoven material or a first part thereof of and the first nonwoven material, or the first part thereof, with the adhesive, to a bonding station;
   e) bonding the first nonwoven material or first part of the first nonwoven material via the construction adhesive to the second nonwoven material or to the first part thereof; wherein the time or distance between steps c) and e) is at least 0.2 seconds or at least 1 meter, respectively.

2. The process of claim 1, wherein in step c) the construction adhesive is applied at an application temperature of at least 120° C., and wherein in the bonding step e) the construction adhesive has a temperature of at least 30° C. less than the application temperature of step c).

3. The process of claim 1 or 2, whereby the first part of the first nonwoven material is or are the peripheral edge or edges thereof, and whereby the first part of the second nonwoven material is or are the peripheral edge or edges thereof, and whereby in step c) the adhesive is applied to the first part of the first nonwoven material and the first part of the first nonwoven material is bonded in step e) to the first part of the second noOnwoven material, and whereby the bond formed by the process are the bonded peripheral edge or edges of the first and second nonwoven materials.

4. The process of claim 3, whereby the first nonwoven material has a second part, adjacent the first part and the second nonwoven material has a second part, adjacent the first part, and the second part of the first nonwoven material and/or the second part of the second nonwoven material carries a superabsorbent material.

5. The process of claim 4, whereby the superabsorbent material is immobilized onto the second part of the second nonwoven material and/or onto the second part of the first nonwoven material by a further adhesive material, applied as fibrous adhesive material over the superabsorbent material after applying the superabsorbent material onto the second part of the nonwoven material and/or onto the second part of the first nonwoven material, and before step e).

6. The process of claim 5, whereby the second part of the first nonwoven material, and optionally the second part of the second nonwoven material comprises no adhesive material, except optionally some of the fibrous adhesive material applied over the superabsorbent material.

7. The process as in claim 5 or 6, whereby the superabsorbent material is sandwiched between the second part of the first nonwoven material and the second part of the second nonwoven material and sealed therein between, by the bonded peripheral edge(s).

8. An absorbent core obtainable by the process of claim 7, the construction adhesive being present substantially around the fibers of the first nonwoven material, or of the first part thereof, but not substantially round the fibers of the second nonwoven material, or of the first part thereof.

9. An absorbent article comprising the absorbent core as in claim 8.

10. The process of claim 1, whereby the first nonwoven is a pattern bonded laminate nonwoven material comprising at least one meltblown nonwoven layer, sandwiched between at least two spunbond nonwoven layers.

11. The process of claim 1, whereby the first nonwoven material comprises fibers that are treated with a hydrophilic agent prior to nonwoven material formation, and/or whereby the nonwoven material of step a) is treated with a hydrophilic agent.

12. The process as in claim 11, whereby the first nonwoven material has a basis weight of 15 g/m$^2$ or less, preferably 12 g/m$^2$ or less.

13. The process as in claim 1, whereby the construction adhesive is selected from the group of block-copolymers having at least styrene blocks and isoprene blocks, block-copolymers having at least styrene blocks and butadiene blocks, metallocene polyolefins or amorphous poly-alpha-olefin polymers.

14. Bonded first and second nonwoven material obtainable by the process of claim 1, the construction adhesive being present substantially around the fibers of the first nonwoven material, or of the first part thereof, but not substantially round the fibers of the second nonwoven material, or of the first part thereof.

* * * * *